US010458906B2

(12) United States Patent
Romero et al.

(10) Patent No.: US 10,458,906 B2
(45) Date of Patent: Oct. 29, 2019

(54) METHOD FOR THE NON-DESTRUCTIVE TESTING OF A CASING

(71) Applicant: Safran Aircraft Engines, Paris (FR)

(72) Inventors: Jean-Louis Romero, Moissy-Cramayel (FR); Angélique Melody Marine Alexia Mainczyk, Moissy-Cramayel (FR); Geoffrey Martin, Moissy-Cramayel (FR)

(73) Assignee: Safran Aircraft Engines, Paris (FR)

( * ) Notice: Subject to any disclaimer, the term of this patent is extended or adjusted under 35 U.S.C. 154(b) by 0 days.

(21) Appl. No.: 15/883,387

(22) Filed: Jan. 30, 2018

(65) Prior Publication Data

US 2018/0217057 A1    Aug. 2, 2018

(30) Foreign Application Priority Data

Jan. 31, 2017 (FR) ..................................... 17 50781

(51) Int. Cl.
| | |
|---|---|
| *G01N 21/35* | (2014.01) |
| *G01N 21/3563* | (2014.01) |
| *G01J 3/433* | (2006.01) |
| *G01N 21/84* | (2006.01) |
| *G01J 3/28* | (2006.01) |
| *G01M 99/00* | (2011.01) |

(52) U.S. Cl.
CPC ........ *G01N 21/3563* (2013.01); *G01J 3/4338* (2013.01); *G01N 21/8422* (2013.01); *G01J 2003/2859* (2013.01); *G01M 99/002* (2013.01); *G01N 2021/8427* (2013.01); *G01N 2021/8472* (2013.01)

(58) Field of Classification Search
CPC .. G01J 3/00; G01J 3/443; G01J 3/4531; G01J 3/4532
See application file for complete search history.

(56) References Cited

U.S. PATENT DOCUMENTS

| | | | |
|---|---|---|---|
| 6,184,528 B1 | 2/2001 | DiMarzio et al. | |
| 2005/0067569 A1* | 3/2005 | Shelley | G01N 21/3563 250/341.8 |

(Continued)

FOREIGN PATENT DOCUMENTS

| | | |
|---|---|---|
| FR | 3 012 218 A1 | 4/2015 |
| WO | WO 2016/087790 A1 | 6/2016 |

*Primary Examiner* — Edwin C Gunberg
*Assistant Examiner* — Mamadou Faye
(74) *Attorney, Agent, or Firm* — Blank Rome LLP

(57) ABSTRACT

A method for the non-destructive testing of the heating of a part made from polymer material, the method comprising the following steps: a) carrying out a measurement by infrared spectroscopy on a part to be tested and extracting therefrom at least one of absorbance values and transmittance values according to a spatial frequency; and b) from the measurement of at least one of absorbance and transmittance, determining the period of time during which said region of the part to be tested has been subjected to a given heating temperature and determining said heating temperature, using a reference database comprising at least one of absorbance measurements and transmittance measurements, the measurements established over a plurality of reference samples made from polymer material that have been subjected to a given temperature during a given period of time.

7 Claims, 2 Drawing Sheets

(56) References Cited

U.S. PATENT DOCUMENTS

| | | | |
|---|---|---|---|
| 2011/0001047 A1 | 1/2011 | Shelley et al. | |
| 2015/0151866 A1* | 6/2015 | Oral ........................ | A61L 27/16 53/425 |
| 2016/0107426 A1* | 4/2016 | Leufgens ................ | C08L 23/06 428/35.2 |

* cited by examiner

US 10,458,906 B2

METHOD FOR THE NON-DESTRUCTIVE TESTING OF A CASING

CROSS-REFERENCE TO RELATED APPLICATIONS

This application claims the benefit of French Patent Application No. 1750781, filed Jan. 31, 2017, the contents of which is incorporated herein by reference.

TECHNICAL FIELD

The present invention relates to a method for the non-destructive testing of a part comprising a matrix, for example made from polymer. In particular, reinforcement fibres may be integrated in the matrix.

BACKGROUND

Conventionally, the upstream end of a turbine engine comprises a fan comprising an impeller formed by a plurality of blades surrounded externally by an annular casing that may be produced from a metal material or a composite material comprising a matrix including reinforcement fibres, such as a polymer matrix, for example epoxy polymer, and reinforcement fibres made from carbon fibres or glass fibres. This casing allows an initial compression of the air entering the turbine engine and also provides a function of confinement of the blades in the event of loss of one of them. The fan casing is surrounded by a plurality of ducts supplying, in particular through a pressurised-air supply duct, at a temperature of around 200° C., equipment of a motor referred to as an APU (auxiliary power unit) used for starting the turbine engine, as well as supplying electricity to the aircraft cabin when the aircraft is on the ground.

In the event of malfunctioning, such as a leakage, of the pressurised-air supply conduit, the air may cause significant local heating of the casing since the temperature of the air is around 200° C. When the casing is produced from metal material, for example aluminium, the heating has no impact on the mechanical integrity of the casing. In the case of a casing with a matrix including reinforcement fibres, its mechanical strength following heating must be able to be guaranteed.

It will therefore be understood that the non-destructive testing of a composite casing with a matrix with reinforcement fibres is particularly important and is all the more so since a composite casing proves to be very expensive.

It has thus been proposed to apply thermosensitive paints to the casing. However, the service life of these paints greatly limits their advantage since an engine may be used for periods greater than the service life of these paints, in particular for aircraft of the long or medium haul type. Furthermore, when an engine is removed, it is subjected in a conventional manner to cleaning by pickling, which causes a total removal of the layer of thermosensitive paint, involving a further step of application of a coat of paint. Finally, though a thermosensitive paint makes it possible to visually note the state of heating of a given region of a casing, it proves to be only an indirect indication of the state of the internal structure of the casing and does not allow precise quantification of the internal structure of the casing.

SUMMARY

The aim of the invention is to afford a simple, effective and economical solution to the problems of the prior art described above.

To this end, it proposes a method for the non-destructive testing of the heating of a part made from polymer material, in particular comprising reinforcement fibres, the method comprising the following steps:

a) carrying out a measurement by infrared spectroscopy at a region of said part to be tested and extracting therefrom the absorbance (or transmittance) values according to the spatial frequency;

b) from the absorbance values, determining an interval of spatial frequencies relating to the oxidation of the polymer of said region of the part;

c) from the measurement of absorbance in said interval of spatial frequencies, determining the period of time during which said region of the part to be tested has been subjected to a given heating temperature and determining said heating temperature, using a reference database comprising absorbance measurements established over a plurality of reference samples made from polymer material, in particular with reinforcement fibres, that have been subjected to a given temperature during a given period of time.

The invention proposes to carry out a direct measurement of the state of the polymer structure of the casing by infrared spectrometry and to compare a parameter obtained from the absorbance measurement with a similar parameter contained in the database.

According to another feature of the invention, the method comprises the following steps:

identifying, in the spatial frequency interval, a first peak for the part to be tested, the amplitude of which depends on the state of oxidation of the polymer of said region of the part to be tested and determining its amplitude, performing step c) by comparing the amplitude of the first peak of the part to be tested with amplitudes of first reference peaks situated in a spatial frequency interval relating to the oxidation of the polymer on said samples and contained in the database.

In a particular embodiment of the invention, the method consists of:

from the absorbance measurement, identifying a second peak for the part to be tested, the amplitude of which is independent of the state of oxidation of the polymer of said region of the part to be tested, and determining the amplitude of the second peak, calculating the ratio of the amplitude value of the first peak obtained on the part to be tested to the amplitude value of the second peak obtained on the part to be tested, performing step c) by comparing said ratio obtained for said region of the part with reference ratios for said samples and contained in databases, each reference ratio for a given sample being calculated by dividing the amplitude of the first reference peak by the amplitude of a second reference peak the amplitude of which is independent of the state of oxidation of the polymer of said sample.

The invention thus proposes to standardise the measurement of the first peak the amplitude of which depends on the level of oxidation at the region in question by a second peak the amplitude of which is independent of the state of oxidation of said region. This standardisation makes it possible to be free from any variations in absorbance that are not due to the region of the part in question but are dependent for example on the measurement conditions, mainly on the surface condition of the material, the sensitivity of the apparatus, the quality of the acquisition, and secondarily the temperature of the environment, the humidity in particular, etc.).

According to yet another feature of the invention, the amplitude of the first peak and the amplitude of the second peak are each, prior to the determination of a ratio in question, corrected by the non-specific absorption variation, which is a function of the emission wavelength of the infrared spectrometer. The non-specific absorption is due to the absorption of part of the incident beam by the polymer or reinforcement, this absorption being related to the depth of penetration in the sample and inversely proportional to the wave number (the spatial frequency). The non-specific absorption therefore causes a deformation of the base line that is not characteristic of any chemical bond.

Taking account of the non-specific absorption on the measurement of the amplitudes of the first and second peaks may prove to be important for the standardisation by the second reference peak to prove to be effective.

The second peak may be chosen so as to be positioned relative to the first peak so that the variation in non-specific absorption between the first peak and the second peak is substantially linear. This facilitates the determination of the non-specific absorption variation between the first and second peaks.

In a particular configuration, the first peak and the second peak are situated in a spatial frequency interval (the wave number $\sigma$, which is the number of oscillations of the wave per unit length, is often referred to as the spatial frequency; it designates the inverse of the wavelength $\lambda$: $\sigma=1/\lambda$; the unit of the wave number is $m^{-1}$) less than 500 $cm^{-1}$ in the vicinity of the ends of which there are determined two absorbance measurements solely relating to non-specific absorption and from which there is determined the linear variation in non-specific absorption as a function of the spatial frequency in order to make the correction to variation in non-specific absorption. It has been found that such a window made it possible to assume linearity in the variation in non-specific absorption in the case of a polymer material with reinforcement fibres. Beyond this width of the spatial frequency interval, it is necessary to consider a polynomial variation in the non-specific absorption.

BRIEF DESCRIPTION OF THE DRAWINGS

The invention will be understood better and other details, advantages and features of the invention will emerge from a reading of the following description given by way of non-limitative example, with reference to the following figures.

DETAILED DESCRIPTION

As explained previously, the casing of the fan produced from polymer, in particular with reinforcement fibres, may in operation undergo local heating that it is necessary to be able to characterise by a non-destructive method making it possible to determine the state of the casing in order to determine whether or not it can be kept in service in a turbine engine.

To this end, the invention that is described with reference to FIGS. 1 to 4 aims firstly to establish a reference database comprising reference absorbance measurements. The term "reference" used below should be understood as designating an element of the reference database comprising the absorbance measurements and more generally the data obtained from reference samples.

Figure 1:
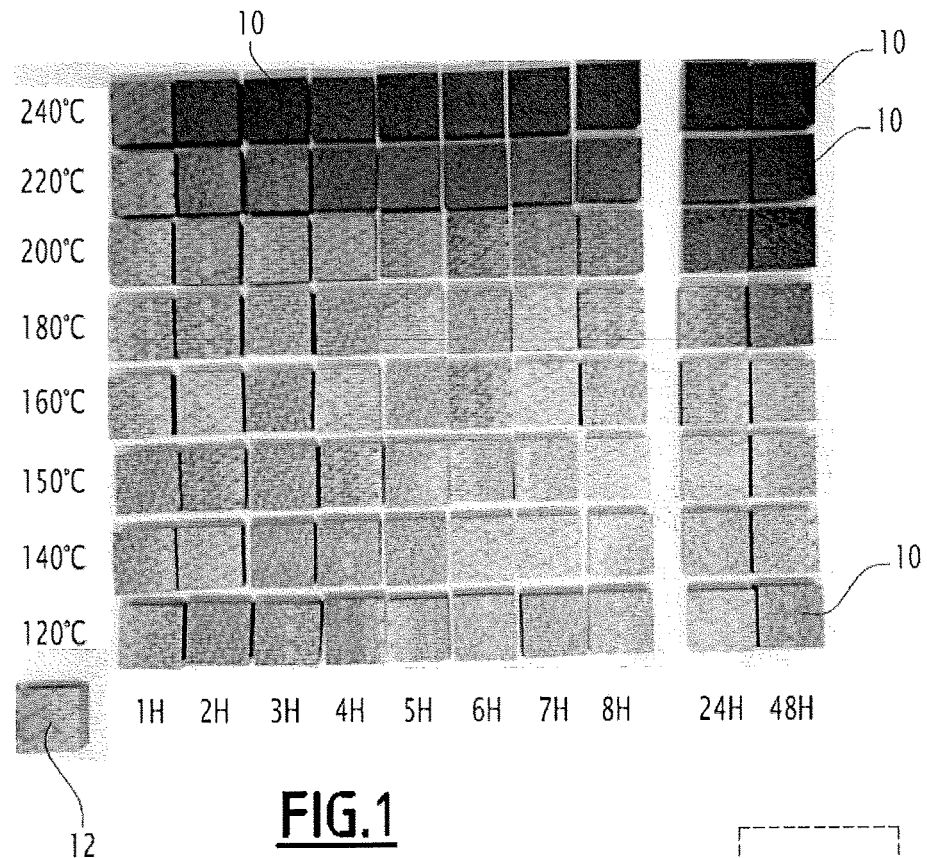
FIG. 1 is a schematic view of a plurality of samples that have each undergone oxidation for a given time (vertically) at a given temperature (horizontally)

For this purpose, a batch of a plurality of samples 10 of a material similar to the part to be analysed is established. FIG. 1 illustrates only part of such a batch, which thus comprises a plurality of samples 10 of a casing made from polymer material with reinforcement fibres arranged in the form of rows and columns. Along a given row, each sample 10 is subjected to a given temperature, the exposure time of which is given by the position along a row. Obviously, the database should comprise a number of samples 10 making it possible to take account of the various oxidation levels that the polymer may suffer under actual operating conditions. Thus the database should comprise samples 10 that have been subjected to the aforementioned temperatures for periods of time ranging up to at least six months.

In the configuration shown by way of example, the samples were subjected to temperatures in ° C. of 120, 140, 150, 160, 188, 200, 220, 240° C. for periods in hours of 1, 2, 3, 4, 5, 6, 7, 8, 24, 48 hours. The sample 12 positioned in the bottom left-hand corner of FIG. 1 represents a sample 12 that has not undergone any heating, which therefore constitutes the absolute reference of a casing without any thermal heating. It can be seen in FIG. 1 that the samples 10 darken as the temperature increases and that the exposure time at a temperature increases, which is consistent with thermal oxidation of the polymer.

Figure 2A:
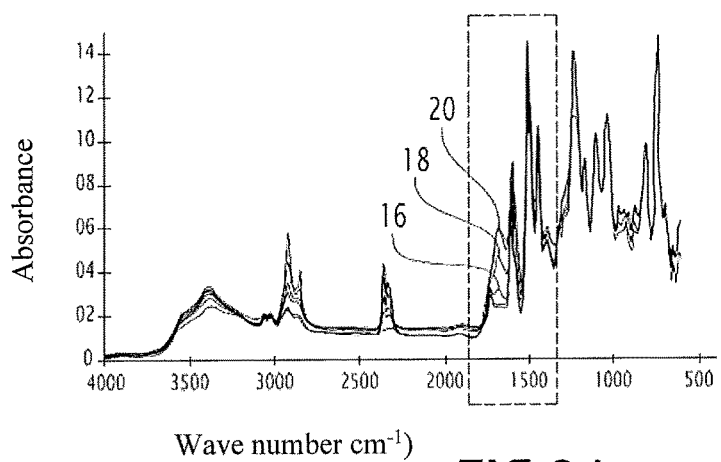
FIG. 2A is a graph showing several absorbance curves as a function of the wave number.

FIG. 2A shows a plurality of absorbance curves as a function of the wave number, obtained for some of the samples 10 in FIG. 1. It will be recalled that the spectroscopic wave number corresponds to the inverse of the wavelength. Firstly, for each absorbance curve as a function of a wave number, it is necessary to identify the wave number interval (or spatial frequency interval) corresponding to the oxidation of the polymer. This spatial frequency interval is generally situated around 1600 $cm^{-1}$ and therein a first reference peak 16, 18, 20 is identified, corresponding specifically to the oxidation of the polymer.

Figure 2B:
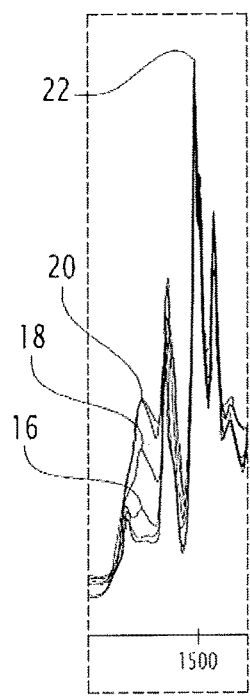
FIG. 2B is an enlargement of the region delimited in broken lines in FIG. 2A.

In FIG. 2A, in the region surrounded by broken lines and centred on 1681 $cm^{-1}$, it is observed that the amplitude of the reference peaks 16, 18, 20 from one sample to another showing clearly the influence of the temperature and time on the oxidation of the polymer (see also FIG. 2B). From the spectroscopic point of view, this position mainly corresponds to the presence of the C=O bond, which relates to the oxidation of the polymer.

As can be seen in FIG. 2B, corresponding to the enlargement of the region delimited in broken lines in FIG. 2A, the absorbance curves also show the presence of a second reference peak 22 situated at 1589 $cm^{-1}$ that is independent of the state of oxidation of the polymer.

The positions of the first and second reference peaks are given by way of indication. This is because these positions are liable to vary according to the sample in question since they are dependent on the chemical bonds studied as well as their environment, and therefore on the chemical nature of the sample studied.

To avoid the variations in amplitude due to the operating conditions (humidity, temperature of the environment when an absorbance measurement is made, in particular) having an impact on the amplitude value measured, it is necessary to standardise the amplitude value of the first reference peak 16, 18, 20 by the amplitude value of the second reference peak 22, for each absorbance curve obtained for a given sample 10. Thus for each sample 10 a ratio $R_{i,j}$ is obtained where i represents the duration of exposure of the sample to a temperature j.

Equally, in FIGS. 2A and 2B, it can be seen that the absence of specific absorbance, that is to say due to a given chemical bond, results in a base absorbance level that is not zero. This absorbance, referred to as non-specific, of a given chemical bond is due to the absorption of the incident infrared beam of the spectrometer used for carrying out the absorbance measurement, this non-specific absorption being a function of the wavelength and increasing therewith.

Thus it is necessary to take into account this non-specific absorption effect in order to increase the relevance of the ratio $R_{i,j}$ for each sample 10. For this purpose, a general approach may consist of deducting, from the amplitude measurement for a given sample 10, the non-specific amplitude value measured for a given peak. However, it proves to be difficult to make this distinction for the first reference peak 16, 18, 20 and the second reference peak 22. Thus it is preferable to determine the function best approximating the variation in non-specific absorption in a reduced window of wave numbers. Thus the method consists of determining the coordinates (wave number; absorbance) of the ends 24a, 24b of an interval 24 of wave numbers comprising the first reference peak 16, 18, 20 and the second reference peak 22 for a given absorbance curve obtained for a given sample 10. Said ends 24a, 24b of the aforementioned wave number interval 24 must not correspond to a specific absorbance, that is to say be related to a particular chemical bond, but on the contrary correspond only to the non-specific absorbance. The simplest approach consists of considering that the variation in the non-specific absorbance is substantially linear in the wave number interval in question comprising the first reference peak 16, 18, 20 and the second reference peak 22. This assumption of linearity is satisfied when the frequency window 24 in question is less than 500 cm$^{-1}$. Thus it is preferable to use a second reference peak 22 situated in the vicinity of the first reference peak 16, 18, 20 in order to make the aforementioned assumption. In the contrary case, it would then be necessary to determine the variation in non-specific absorbance by taking into account the non-linearity of this variation.

From the equation of the straight line passing through the two ends 24a, 24b of said interval 24, it is consequently possible to determine the non-specific absorbance value for the wave number corresponding to the position of the first reference peak 16, 18, 20 and the absorbance value for the wave number corresponding to the position of the second reference peak 22, and to subtract them from the measured total absorbance value previously measured. Next the ratio $R_{i,j}$ is calculated from these new corrected absorbance amplitude values from the non-specific absorption values.

Figure 4:
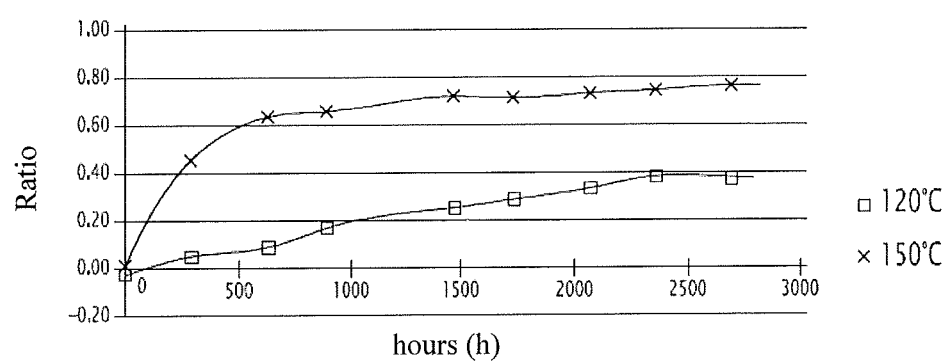
FIG. 4 is a graph showing the change in a given ratio as a function of time.

Thus it will be understood that the reference database consists of a plurality of values $R_{i,j}$ each in relation to a given sample 10. From the various ratio values $R_{i,j}$, it is possible to establish the graph shown in FIG. 4 showing the change in the ratio $R_{i,j}$ as a function of the time of exposure of the samples to a given temperature, each curve corresponding to a given heating temperature. Only two curves, the one corresponding to 120° C. and the one corresponding to 150° C., are shown in FIG. 4.

Figure 3:
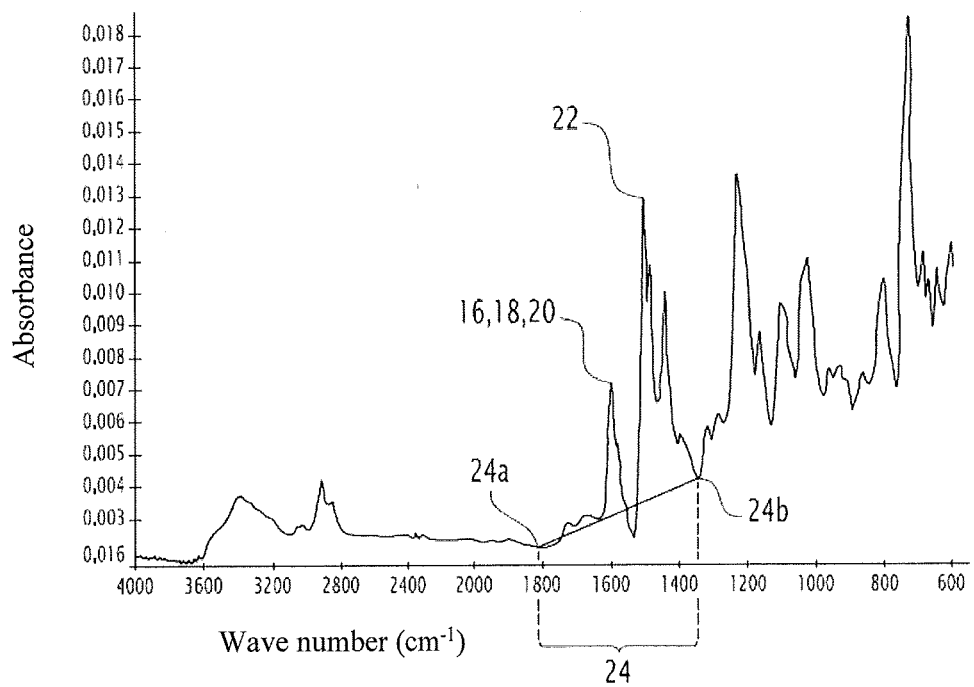
FIG. 3 is a graph showing the change in the absorbance as a function of the wave number and comprising the trace of a line determining the non-specific absorbance.

Thus, when a given region of a part such as a casing must be tested, an operator makes a measurement of absorbance by means of an infrared spectrometer and makes a determination of the ratio R in the same way as described above for a sample in the reference database in relation to FIGS. 1, 2 and 3. From the measurement of the ratio R for the given region of the part to be tested, the ratio is compared with the ratio values contained in the reference database using the curve given in FIG. 4. Thus it will be understood that, for a value R, it is possible to establish a unique intersection with a single curve, this curve thus giving information to the operator about the temperature to which the tested region of the part has been subjected and the X axis indicating the exposure time.

It should be noted that, below a threshold H, which may for example be 24 hours, the data do not appear to be usable.

For temperature curves that are spaced apart, for example, at a step of 10° C., it will be understood that for a measured value R it is possible to move the ordinate straight line corresponding to a measurement point R closer to the closest curve, or the most detrimental one (safety factor) according to the confidence coefficient sought, this curve thus giving the operator information on the temperature to which the tested region of the part has been subjected and the X axis indicating the exposure time.

In an example embodiment, a ratio of 0.6 corresponds to the limit beyond which the part must be scrapped and is no longer, in its present condition, suitable for being used. If the ratio is below 0.6 the part is considered to be usable and above 0.6 the resin degrades by pyrolysis.

The invention claimed is:

1. A method for non-destructive testing of a heating of a part made from polymer material, the method comprising:
    a) carrying out a measurement by infrared spectroscopy at a region of said part to be tested and extracting therefrom test values comprising at least one selected from the group of absorbance values and transmittance values according to a spatial frequency;
    b) from test values, determining an interval of spatial frequencies relating to an oxidation of a polymer of said region of the part; and
    c) from the test values in said interval of spatial frequencies, determining a period of time during which said region of the part to be tested has been subjected to a given heating temperature and determining said given heating temperature, using a reference database comprising sample values including at least one selected from the group of absorbance measurements and transmittance measurements, the sample values established over a plurality of reference samples made from polymer material that have been subjected to a given temperature during a given period of time, both the given temperature and the given period of time varying among the plurality of reference samples so as to cover a plurality of periods of time and a plurality of temperatures.

2. The method of claim 1, further comprising:
    identifying, in the interval of spatial frequencies, a first peak for the part to be tested, an amplitude of which depends on a state of oxidation of the polymer of said region of the part to be tested and determining an amplitude value of the first peak,
    performing step c) by comparing the amplitude value of the first peak of the part to be tested with amplitude values of first reference peaks situated in a spatial frequency interval relating to the oxidation of the polymer on said reference samples and contained in the reference database.

3. The method of claim 2, further comprising:

from test values, identifying a second peak for the part to be tested, an amplitude of which is independent of the state of oxidation of the polymer of said region of the part to be tested, and determining an amplitude value of the second peak, calculating a ratio R of the amplitude value of the first peak obtained on the part to be tested to the amplitude value of the second peak obtained on the part to be tested, performing step c) by comparing said ratio obtained for said region of the part with reference ratios $R_{i,j}$ for said reference samples and contained in the reference database, each reference ratio $R_{i,j}$ for a given sample being calculated by dividing an amplitude value of a first reference peak by an amplitude value of a second reference peak, the amplitude of which is independent of the state of oxidation of the polymer of said given sample.

4. The method of claim 3, wherein the amplitude value of the first peak of the part to be tested and the amplitude value of the second peak of the part to be tested are each, prior to a determination of a ratio in question, corrected by a variation in non-specific absorption that is a function of an emission wavelength of an infrared spectrometer used to carry out the measurement of the region of the part to be tested.

5. The method of claim 4, wherein the second peak of the part to be tested is chosen so as to be positioned relative to the first peak of the part to be tested so that the variation in non-specific absorbance between the first peak and the second peak is substantially linear.

6. The method of claim 5, wherein the first peak of the part to be tested and the second peak of the part to be tested are situated in a spatial frequency interval of less than 500 $cm^{-1}$, wherein near ends of the spatial frequency interval there are determined two absorbance measurements solely relating to non-specific absorption and from which there is determined the linear variation in non-specific absorption as a function of the spatial frequency in order to make the non-specific absorption variation correction.

7. The method of claim 1, wherein the polymer material comprises reinforcement fibres.

* * * * *